(12) United States Patent
Kaneko

(10) Patent No.: US 6,503,739 B1
(45) Date of Patent: Jan. 7, 2003

(54) PROCESSES FOR PRODUCING S,S-2-HYDROXYPROPYLENEDIAMINE-N-N'-DISUCCINIC ACID

(75) Inventor: Makoto Kaneko, Yokohama (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 0 days.

(21) Appl. No.: 09/926,386

(22) PCT Filed: Apr. 26, 2000

(86) PCT No.: PCT/JP00/02744

§ 371 (c)(1),
(2), (4) Date: Oct. 24, 2001

(87) PCT Pub. No.: WO00/65079

PCT Pub. Date: Nov. 2, 2000

(30) Foreign Application Priority Data

Apr. 27, 1999 (JP) .............................................. 11-119474

(51) Int. Cl.⁷ ............................. C12P 13/04; C12P 1/00; C12P 13/00; C07C 229/00
(52) U.S. Cl. ........................ 435/106; 435/42; 435/128; 562/565
(58) Field of Search ............................. 562/565; 435/42, 435/106, 128

(56) References Cited

U.S. PATENT DOCUMENTS 5,531,915 A * 7/1996 Perkins ...................... 510/294
5,939,296 A * 8/1999 Sakano et al. ............... 435/145
6,103,508 A * 8/2000 Kato et al. ................... 435/184

FOREIGN PATENT DOCUMENTS

| EP | 0 731 171 | 9/1996 |
|---|---|---|
| EP | 0 805 211 | 11/1997 |
| EP | 0 845 536 | 6/1998 |
| JP | 8-51989 | 2/1996 |
| JP | 8-165271 | 6/1996 |
| JP | 9-289895 | 11/1997 |
| JP | 10-218846 | 8/1998 |
| WO | WO 94/20599 | 9/1994 |

* cited by examiner

Primary Examiner—Richard L. Raymond
Assistant Examiner—Zachary C. Tucker
(74) Attorney, Agent, or Firm—Oblon, Spivak, McClelland, Maier & Neustadt, P.C.

(57) ABSTRACT

Provided is an industrially advantageous process for producing S,S-2-hydroxypropylenediamine-N,N'-disuccinic acid which does not use expensive optically active substances. S,S-2-hydroxypropylenediamine-N,N'-disuccinic acid is stereospecifically produced from fumaric acid and 2-hydroxypropylenediamine by the action of ethylenediamine disuccinic acid ethylenediamine lyase (EDDS-ase) or from maleic acid and 2-hydroxypropylenediamine by combining the action of EDDS-ase with the action of maleic acid isomerase.

22 Claims, No Drawings

PROCESSES FOR PRODUCING S,S-2-HYDROXYPROPYLENEDIAMINE-N-N'-DISUCCINIC ACID

This application is a National Stage filing under 35 U.S.C. 371 of PCT/JP00/02744, published as WO 00/65079, published Feb. 11, 2000.

TECHNICAL FIELD

The present invention relates to a process for producing S,S-2-hydroxypropylenediamine-N,N'-disuccinic acid by making use of the action of a lyase possessed by a microorganism.

S,S-2-Hydroxypropylenediamine-N,N'-disuccinic acid is a compound which is expected to be used in the fields of photography, detergents, paper making, etc. as a biodegradable chelating agent.

BACKGROUND ART

As to a process for producing 2-hydroxypropylenediamine-N,N'-disuccinic acid (hereinafter abbreviated as HPDDS), there have been disclosed a process for producing its stereoisomer mixture (a mixture of meso-compound and racemic modification) from maleic acid and 2-hydroxypropylenediamine (alias: 1,3-diamino-2-propanol) (cf. U.S. Pat. No. 3,158,635) and a process for producing its optically active S,S-isomer from S-aspartic acid, which is an optically active substance, and 1,3-dichloro-2-propanol (cf. Zhurnal Obshuchei Khimii, Vol. 49, p. 663, 1979). Further, it is known that among the three isomers of S,S-, R,R- and meso-, only the S,S-isomer is easily biodegradable (cf. JP-A-8-507805).

DISCLOSURE OF THE INVENTION

On the other hand, the present inventors have previously found a novel lyase activity of a microorganism which catalytically converts fumaric acid and ethylenediamine into S,S-ethylenediamine-N,N'-disuccinic acid (said lyase being hereinafter designated as ethylenediamine disuccinic acid ethylenediamine lyase and abbreviated as EDDS-ase) and proposed an economical and efficient process for producing an optically active aminopolycarboxylic acid which makes use of the above-mentioned catalytic action (cf. JP-A-9-140390). The inventors have further developed various technologies regarding the process for producing such optically active aminopolycarboxylic acids (cf., for example, JP-A-9-289895, JP-A-10-52292, JP-A-10-218846 and JP-A-10-271999). However, in almost all cases, an enzyme has a strict substrate specificity, and it has been utterly unknown whether HPDDS can be synthesized by the action of EDDS-ase or not.

The object of the present invention is to provide an economically advantageous process for producing S,S-HPDDS which does not use an expensive optically active substance.

The present inventors have made extensive study to attain the above-mentioned object and resultantly found that, by the action of EDDS-ase, S-2-hydroxypropylenediamine-N-monosuccinic acid is synthesized from one molecule of fumaric acid and one molecule of 2-hydroxypropylenediamine and further one molecule of fumaric acid reacts thereto, whereby S,S-HPDDS can be synthesized stereospecifically, and that S,S-HPDDS can be similarly synthesized from maleic acid and 2-hydroxypropylenediamine by combining the above-mentioned action of EDDS-ase with the action of maleic acid isomerase. The present invention has been accomplished on the basis of the above findings.

Thus, according to the present invention, there are provided (1) a process for producing S,S-2-hydroxypropylenediamine-N,N'-disuccinic acid which comprises producing S,S-2-hydroxypropylenediamine-N,N'-disuccinic acid, in an aqueous medium containing fumaric acid and 2-hydroxypropylenediamine as substrates, from said substrates by the action of ethylenediamine disuccinic acid ethylenediamine lyase of a microorganism origin, (2) a process for producing S,S-2-hydroxypropylenediamine-N,N'-disuccinic acid which comprises producing S,S-2-hydroxypropylenediamine-N,N'-disuccinic acid, in an aqueous medium containing maleic acid or maleic anhydride and 2-hydroxypropylenediamine as substrates, from said substrates by combined actions of ethylenediamine disuccinic acid ethylenediamine lyase and maleic acid isomerase each of a microorganism origin, (3) the process for producing S,S-2-hydroxypropylenediamine-N,N'-disuccinic acid described in (1) or (2) above wherein at least one metal ion selected from the group consisting of alkaline earth metals, iron, zinc, copper, nickel, aluminum, titanium and manganese is made to exist in the aqueous medium containing the substrates, (4) the process for producing S,S-2-hydroxypropylenediamine-N,N'-disuccinic acid described in (3) above wherein the metal ion is at least one metal ion selected from the group consisting of magnesium, manganese and iron, (5) the process for producing S,S-2-hydroxypropylenediamine-N,N'-disuccinic acid described in (1) or (2) above wherein a content of R-2-hydroxypropylenediamine-N-monosuccinic acid contained as an impurity in the aqueous medium containing the substrates is 2.5% by mole or less of the theoretical value of S,S-2-hydroxypropylenediamine-N,N'-disuccinic acid to be formed, (6) a process for producing an S,S-2-hydroxypropylenediamine-N,N'-disuccinic acid alkali metal salt which comprises adding an alkali hydroxide to the reaction product mixture obtained in (3) or (4) described above to separate and recover as an insoluble precipitate the metal ions, which had been made to exist, and simultaneously to convert the S,S-2-hydroxypropylenediamine-N,N'-disuccinic acid into its alkali metal salt, (7) the process for producing S,S-2-hydroxypropylenediamine-N,N'-disuccinic acid described in (3) or (4) above wherein the separated and recovered insoluble precipitate is reused as a metal ion source, (8) the process for producing S,S-2-hydroxypropylenediamine-N,N'-disuccinic acid described in any of (1) to (5) above which comprises adding at least one organic acid selected from the group consisting of fumaric acid, maleic acid and maleic anhydride to the reaction product mixture, recovering S,S-2-hydroxypropylenediamine-N,N'-disuccinic acid or its salt as an insoluble substance and reusing the resulting supernatant for the reaction, (9) the process for producing S,S-2-hydroxypropylenediamine-N,N'-disuccinic acid described in any of (1) to (5) above which further includes the step of precipitating and recovering S,S-2-hydroxypropylenediamine-N,N'-disuccinic acid as crystalline powder from the reaction product mixture under an acidic condition by use of a mineral acid,

(10) a crystalline powder of S,S-2-hydroxypropylenediamine-N,N'-disuccinic acid in which the sum of contents of cyclic compounds represented by the following structural formulas [1] and [2] is 1% by mole or less relative to S,S-2-hydroxypropylenediamine-N,N'-disuccinic acid,

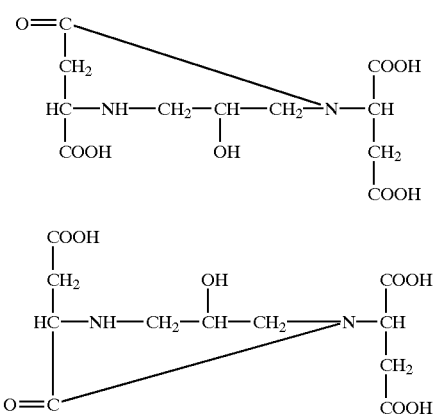

(11) the process for producing S,S-2-hydroxypropylenediamine-N,N'-disuccinic acid described in (1) above wherein the ethylenediamine disuccinic acid ethylenediamine lyase originates from a microorganism belonging to the genus Brevundimonas, the genus Paracoccus, the genus Sphingomonas, the genus Acidovorax, the genus Pseudomonas or the genus Burkholderia or from a microorganism transformed by a gene DNA which codes ethylenediaminedisuccinic acid ethylenediamine lyase of these microorganisms origin, and

(12) the process for producing S,S-2-hydroxypropylenediamine-N,N'-disuccinic acid described in (2) above wherein the ethylenediamine disuccinic acid ethylenediamine lyase originates from a microorganism belonging to the genus Brevundimonas, the genus Paracoccus, the genus Sphingomonas, the genus Acidovorax, the genus Pseudomonas or the genus Burkholderia or from a microorganism transformed by a gene DNA which codes ethylenediamine disuccinic acid ethylenediamine lyase of these microorganisms origin and the maleic acid isomerase originates from a microorganism belonging to the genus Alcaligenes, the genus Pseudomonas, the genus Xanthomonas or the genus Bacillusor or from a microorganism transformed by a gene DNA which codes maleic acid isomerase of these microorganisms origin.

BEST MODE FOR CARRYING OUT THE INVENTION

Cultivation of Microorganism

The microorganisms used in the present invention are as described later.

The kind of culture media for the microorganism used in the present invention is not particularly limited and both a synthetic medium and a natural medium may be used so long as they appropriately contain an assimilable carbon source, nitrogen source, inorganic salt and further a slight amount of an organic nutrient. When obtaining strain cells having a high activity is desired, for example, in the case of microorganisms having an EDDS-ase activity, an amino acid such as HPDDS, ethylenediamine-N,N'-disuccinic acid, ethylenediamine-N-monosuccinic acid, aspartic acid, glutamic acid and histidine or fumaric acid etc. is added to the culture medium and, in the case of microorganisms having a maleic acid isomerase activity, maleic acid and the like is added to the medium. The cultivation conditions may vary depending on the strain cells and the culture medium. The pH of the culture medium is in the range of preferably from 4 to 10, more preferably from 6 to 9. The cultivation temperature is preferably 20–40° C., but in the case of a thermophilic microorganism such as those of the genus Bacillis, a cultivation temperature of about 50–70° C. may be used in some cases. The cultivation is conducted until the activity reaches the maximum, if necessary with aeration and/or stirring.

Removal of Fumarase Activity of Microorganism

Removal of the fumarase activity present in microorganisms may be conducted for strain cells or a substance obtained by treating the strain cells (in the present description, refers to disrupted strain cells, strain cell extract, an extracted crude or purified enzyme, imobilized strain cells or enzyme, and strain cells or enzyme subjected to a treatment with chemicals (e.g. stabilizing treatment)) at a treating pH in the range of preferably from 8 to 10.5, more preferably from 8.5 to 10, at a treating temperature preferably in the range of from freezing temperature to 55° C. and for a period of time not particularly limited (cf. JP Application No. 9-311046).

S,S-HPDDS Producing Reaction

A reaction for producing S,S-HPDDS is preferably conducted by bringing strain cells or a substance obtained by treating the strain cells, in an aqueous medium containing fumaric acid and 2-hydroxypropylenediamine of substrates and, according to necessity, metal compounds, which serve as the source of metal ions that participate in the reaction, and salts etc. having a buffering ability to be added for stabilizing the enzyme, into contact with the substrates, but it may also be conducted by adding fumaric acid, 2-hydroxypropylenediamine and said metal compound directly to the strain cell culture broth.

The reaction is conducted in the temperature range of preferably from 0° C. to 60° C., more preferably from 20° C. to 45° C., and in the pH range of preferably 4–11, more preferably 7–10. The concentration of fumaric acid used in the reaction is preferably 0.01–3M (mol/l) though it varies depending on the reaction temperature and pH; the presence of the acid as a precipitate due to its concentration exceeding the saturation solubility is permissible because the precipitate goes into solution with the progress of the reaction. The concentration of 2-hydroxypropylenediamine is preferably 0.01–2M.

The forming ratio of S-2-hydroxypropylenediamine-N-monosuccinic acid, which is an intermediate of the present reaction, to S,S-HPDDS can be varied according to necessity by varying the molar ratio of fumaric acid to 2-hydroxypropylenediamine. In this case, the forming ratio of S-2-hydroxypropylenediamine-N-monosuccinic acid increases when the ratio of 2-hydroxypropylenediamine to fumaric acid is increased.

The amount of the microorganism or the like to be used is preferably 0.01–5% by weight in terms of dry strain cells relative to the substrate.

Irrespective of whether the starting material concerned is 2-hydroxypropylenediamine or fumaric acid, a reaction system which can synthesize the two starting materials from other compounds can be made to coexist with the present system so long as an effect which constitutes the gist of the present invention can be obtained.

When maleic acid isomerase is made to coexist in the reaction, maleic acid or its salt can be used as a substrate in place of the above-mentioned fumaric acid. Maleic anhydride can be used similarly because it is easily converted into maleic acid in an aqueous solution. The conditions for such reactions are generally similar to those wherein fumaric acid is used as the starting material, though in some cases they vary depending on EDDS-ase which is made coexistent.

Reaction in the Presence of Metal Ion

The present reaction is an equilibrium reaction and seemingly stops in the middle thereof. Thus, the equilibrium can be shifted to the product side and the yield can be improved by making present in the reaction system a polyvalent metal ion which can be coordinated to S,S-HPDDS.

The metal ion in the present invention is not particularly limited so long as it is a metal ion which can be chelated to S,S-HPDDS to form a complex. It may be, for example, ions of simple elements of heavy metals and alkaline earth metals or ions of coordination compounds. Specific examples thereof include ions of heavy metals such as $Fe(II)$, $Fe(III)$, $Zn(II)$, $Cu(II)$, $Ni(II)$, $Co(II)$, $Al(III)$, $Mn(II)$ and $Ti(IV)$; and ions of alkaline earth metals such as $Mg(II)$, $Ca(II)$ and $Ba(II)$. In actual practice, it is preferable to add hydroxides, oxides and their salts, and compounds with sulfuric acid, hydrochloric acid, nitric acid, acetic acid and carbonic acid of these metal ions. Accordingly, even when these compounds are present in the reaction mixture in the form of ions comprising a metal or a non-metallic element or such ions are generated after the addition, they are usable so long as they can coordinate with S,S-HPDDS and can give the intended effect of the present invention. These ions or compounds may be used in a combination of two or more thereof.

Some of the metal compounds or the salts comprising the metal compound and fumaric or maleic acid have a low solubility. However, the presence of such compounds or salts over saturation, that is, in the form of suspension, is permissible because S,S-HPDDS which is formed with the progress of reaction will chelate therewith thereby to yield the intended effect of the present invention. These metal compounds may be added either in a lump at the initiation of the reaction or in the course of the reaction.

The amount of the metal compound used as the metal source and added to the reaction mixture is preferably 0.01–2 times by mole the amount of S,S-HPDDS formed.

In controlling the pH, when a metal ion is not added or when an alkaline earth metal is added, since the pH tends to decrease, the pH control can be done with an alkali such as alkali metal hydroxides, 2-hydroxypropylenediamine and alkali metal salt or ammonium salt of S,S-HPDDS, and when an ion of a metal other than alkaline earth metals is added, since the pH tends to increase, it can be done with an acid such as sulfuric acid, hydrochloric acid, nitric acid, phosphoric acid, fumaric acid, maleic acid and S,S-HPDDS.

When the metal complex of S,S-HPDDS is required, the intended compound can be directly obtained, after conducting the reaction in the presence of a predetermined metal ion, through operations of pH control, concentration, etc. On the other hand, for collecting S,S-HPDDS from the reaction product mixture, it can be effected by conducting an acid precipitation as described later. However, in a system wherein a complex which is stable at the pH of the acid precipitation has been formed, for example in the case that the reaction has been conducted in the presence of a heavy metal ion such as an iron ion, said metal ion needs to be removed prior to the acid precipitation. Therefore, when S,S-HPDDS is needed, it is effective to conduct the reaction in the presence of an ion of alkaline earth metals such as magnesium and calcium, which does not need the above-mentioned removal operation, at the time of acid precipitation.

The effect of the metal ion addition is thought to be attributed to the shift of the chemical equilibrium point from the substrate side to the product side caused by the metal ion. Since, in general, a chemical equilibrium point is independent on the kind of a catalyst, the chemical equilibrium point in the present invention shows a constant value for all catalysts so long as it is not affected by a side reaction or other reactions. Therefore, the effect of the metal ion addition is not particularly related to which microorganism is the origin of the EDDS-ase of the catalyst.

Suppression of Meso-HPDDS Formation During Reaction

In the reaction product mixture as it is or when an aqueous alkali metal salt solution is needed as described later, a contamination by meso-HPDDS is usually unfavorable because not only it lowers a chemical purity of intended S,S-HPDDS but also the meso-isomer is poor in biodegradability as compared with S,S-HPDDS as mentioned above.

As to the cause of meso-HPDDS contamination, the following schema is supported by experimental facts. First, racemic modification of 2-hydroxypropylenediamine-N-monosuccinic acid is formed from fumaric or maleic acid and 2-hydroxypropylenediamine without the aide of a microorganism catalyst. Then, of two optical isomers of S and R, R-hydroxypropylenediamine-N-monosuccinic acid reacts with fumaric acid through the catalytic action of EDDS-ase to form meso-HPDDS (the S-isomer is converted to S,S-HPDDS).

The above-mentioned formation of the racemic-2-hydroxypropylenediamine-N-monosuccinic acid is the more marked when the temperature is the higher, the pH is the higher, the substrate concentration is the higher and the period of time of an exposure of the substrate to these conditions is the longer. The formation is particularly marked when the substrate concentration is high; in other words, the racemic compound is mainly formed during the preparation of the aqueous substrate solution rather than during the reaction. That is, the contamination by meso-HPDDS can be markedly suppressed if the formation of the racemic-2-hydroxypropylenediamine-N-monosuccinic acid during the preparation of the aqueous substrate solution is suppressed. Desirably, the content of R-2-hydroxypropylenediamine-N-monosuccinic acid in the aqueous substrate solution is controlled to 2.5% by mole or less of the theoretical value of S,S-2-hydroxypropylenediamine-N,N'-disuccinic acid to be formed.

Recovery and Recycle Use of Metal in Adding Reaction of Metal Ion, and Production of S,S-HPDDS Alkali Metal Salt After a completion of the reaction, the strain cells or the substance obtained by treating the strain cells are removed by filtration or centrifugation, etc., then an alkali hydroxide such as sodium hydroxide and potassium hydroxide is added thereto until the metal ion becomes insolubilized, and the insolubilized precipitate is removed by a conventional means for solid-liquid separation, such as filtration or centrifugation, whereby S,S-HPDDS alkali metal salt can be obtained as a supernatant. The recovered precipitate can be reused as the metal ion source in the above-mentioned reaction.

The amount of the alkali hydroxide to be used is preferably 2–6 times by mole equivalent, more preferably 3–4.5 times by mole equivalent, in terms of the final concentration in the reaction mixture (including the amount added during the preparation of the substrate solution or during the reaction), of the amount of S,S-HPDDS contained in the reaction mixture, though it may vary depending on the kind of metal ions used in the reaction. The alkali hydroxide may be used in a mixture of two or more kinds thereof or in a combination with other alkalis.

In adding the alkali hydroxide, when it is added at once in a short time, the precipitating insolubilized product tends to become fine particles and difficult to separate; however, an addition over a sufficiently long period of time is preferable because particles with good sedimentation property are obtained thereby. Both when the alkali hydroxide is added to the reaction product mixture or, conversely, when the reaction product mixture is added to the alkali hydroxide, a solidification will take place at the instant when liquid drop added comes into contact with the other liquid, so that a uniformity in the vessel tends to be difficult to be maintained, particle diameters tend to be non-uniform, and too fine particles tend to be formed. As a more recommendable procedure for such a case, the reaction product mixture and the alkali hydroxide are fed together into a suitable crystallization vessel and, preferably, the simultaneous feeding and withdrawing of the slurry from the vessel are conducted continuously, whereby relatively large particles of improved separability can be obtained.

Acid Precipitation and Recovery of S,S-HPDDS by Use of Fumaric Acid or Maleic Acid and Recycle Use of Supernatant The acid precipitation of S,S-HPDDS can be conducted by using fumaric acid or maleic acid (including maleic anhydride and substances obtained by treating it), which are the substrates of the reaction. The conditions for the acid precipitation are selected from ranges wherein S,S-HPDDS precipitates and these substrates are dissolved because the acid precipitation is intended for S,S-HPDDS recovery and, at the same time, for the recycle use of the supernatant in the reaction. The amount of fumaric acid or maleic acid to be added is preferably 0.2–3 times by mole, more preferably 0.8–2.4 times by mole, of the amount of S,S-HPDDS. The temperature is controlled in the range of preferably from about 0° C. to about 80° C., more preferably from 10° C. to 60° C., by if necessary gradually cooling the slurry after a part of the S,S-HPDDS has been precipitated or seed crystals of S,S-HPDDS have been added. When the reaction is conducted as a continuous process, under the conditions as described above, fumaric acid or maleic acid and the above-mentioned reaction product mixture may be fed so as to give a residence time of preferably from about 0.5 to about 10 hours, more preferably from 1 to 5 hours, and the S,S-HPDDS crystal slurry obtained can be withdrawn continuously or intermittently.

The precipitated crystals can be collected by conventional means such as filtration and centrifugation. Subsequently, salts in crude crystals formed at the time of acid precipitation and cyclized products described later are washed away by using water or an organic solvent. The method for the washing also is not particularly limited and can be conventional ones such as linsing and slurry washing.

Wet crystals obtained after washing is dried preferably at a temperature so as to keep a product temperature of not higher than 80° C.

Supernatant obtained after the recovery of S,S-HPDDS can be reused for the above-mentioned reaction after having been mixed with a specified amount of 2-hydroxypropylenediamine and an acid, alkali, etc. for pH control.

Acid Precipitation and Recovery of S,S-HPDDS by Use of Mineral Acid

For the crystallization, the above-mentioned reaction product mixture or an aqueous S,S-HPDDS alkali metal salt solution or a concentrated product thereof etc. are, in the case of conducting in a batch process, conditioned to a pH range of preferably from about 1.8 to about 4.5, more preferably from 2.0 to 4.0 by using a mineral acid such as sulfuric acid and hydrochloric acid and to a temperature range of preferably from about 40° C. to about 80° C., more preferably from 40° C. to 60° C., and, if necessary a part of the S,S-HPDDS has been precipitated or seed crystals of S,S-HPDDS have been added, and then it is gradually cooled. The cooling temperature is preferably not higher than about 40° C., more preferably 30° C. to 0° C. When the crystallization is conducted in a continuous process, the initial charge of the above-mentioned reaction product mixture, etc. is conditioned to a pH range of preferably from about 1.8 to about 4.5, more preferably from 2.0 to 4.0 and a temperature range of preferably from 0° C. to 40° C., then the mineral acid and the above-mentioned reaction product mixture and an aqueous S,S-HPDDS alkali metal salt solution or a concentrated product thereof etc. are fed so as to give a residence time of preferably from about 0.5 to about 10 hours, more preferably from 1 to 5 hours, though the residence time may vary depending on the conditions of pH and temperature, and the resulting S,S-HPDDS slurry is withdrawn continuously or intermittently.

Though the pH increases along with the precipitation of the crystals, pH may be adjusted, according to necessity, to a predetermined value by use of a mineral acid such as sulfuric acid and hydrochloric acid. When the crystallization pH is selected to about 4 or above, S,S-HPDDS tends to precipitate as salt of cations contained in the reaction mixture. Since such salts have sometimes their own merits that, for example, a mono-sodium salt of S,S-HPDDS has more affinity for water than S,S-HPDDS itself, the pH may be changed according to necessity to obtain an intended salt.

On the other hand, cyclized products originated from HPDDS represented by the following structural formulas [1] and [2] tend to be formed the more easily as the pH is the lower and the temperature is the higher and the time of exposure to these conditions is the longer. The formation of the cyclized products results in a decrease of a recovery rate of S,S-HPDDS crystals. Moreover, the cyclized products remaining in the supernatant adhere to the crystals to result in a cause for a lowering of the quality of the intended product. An adoption of the conditions described above as preferable can keep the formation of the cyclized product at a less extent. According to the present acid precipitation method, the crystals of S,S-HPDDS can be ultimately obtained in a yield of 90% or more.

Collection and drying etc. of the precipitated crystals can be conducted in the same manner as described for the above-mentioned acid precipitation using fumaric acid and maleic acid.

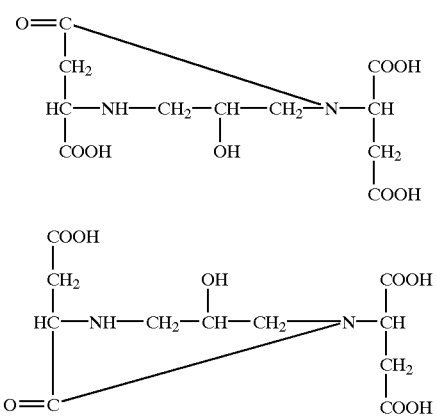

Microorganism Having EDDE-ase

Examples of the microorganism having an EDDS-ase activity include microorganisms belonging to the genus Burkholderia, the genus Acidovorax, the genus Pseudomonas, the genus Paracoccus, the genus Sphingomonas and the genus Brevundimonas, and further transformants obtained by introducing a gene which codes EDDS-ase into a microorganisms belonging to the genus Esherichia or the genus Rhodococcus used as a host.

Specific examples include Burkholderia sp. KK-5 (FERM BP-5412), Burkholderia sp. KK-9 (FERM BP-5413), Acidovorax sp. TN-51 (FERM BP-5416), Pseudomonas sp. TN-131 (FERM BP-5418), Paracoccus sp. KK-6 (FERM BP-5415), Paracoccus sp. TNO-5 (FERM BP-6547), sphingomonas sp. TN-28 (FERM BP-5419), Brevundimonas sp. TN-30 (FERM BP-5417) and Brevundimonas sp. TN-3 (FERM BP-5886) and further transformants obtained by using *Escherichia coli* JM109 [*Escherichia coli* ATCC 53323] or *Rhodococcus rhodochrous* ATCC 17895 as a host.

Among the above-mentioned microorganisms, the strains KK-5, KK-9, TN-51, TN-131, KK-6, TN-28, TN-30 and TN-3 were newly isolated from the natural world by the present inventors and have been deposited with National Institute of Bioscience and Human Technology, Agency of Industrial Science and Technology, Ministry of International Trade and Industry (Higashi 1-1-3, Tsukuba-shi, Ibaraki-ken, Japan (postal code number 305-8566)) under the above-mentioned accession numbers. The mycological properties of these strains are also described in the above-mentioned JP-A-9-140390 and JP-A-10-52292.

The strain TNO-5 was also newly isolated from the natural world by the present inventors and has been deposited with the above-mentioned National Institute of Bioscience and Human Technology, Agency of Industrial Science and Technology, Ministry of International Trade and Industry under the above-mentioned accession number. Bachteriological properties thereof are as follows.

| Bacteriological properties | |
|---|---|
| Morphology | TNO-5 strain sherical-short bacillus |
| Gran staining | – |
| Spore | – |
| Motility | – |
| Attitude to oxygen | aerobic |
| Oxidase | + |

| Bacteriological properties | |
|---|---|
| Catalase | + |
| OF test | – |
| Color of colony | Forming no characteristic pigment |
| Accumulation of PHB | + |
| Reduction of nitrate | – |
| Reduction of nitrite | – |
| Quinone type | Q-10 |
| GC content of DNA (mol %) | 65 (HPLC method) |

As a result of classification based on the above-mentioned bacteriological properties according to the description given in Bergey's Manual of Systematic Bacteriology, Vol. 9 (1990), the strain TNO-5 was identified as a bacterium belonging to the genus Paracoccus. Incidentally, it has been confirmed that the strain TN-3 belongs to the diminuta sp.

The strain *Esherichia coli* JM109 (*Esherichia coli* ATCC53323 strain) and the strain *Rhodococcus rhodochrous* ATCC17895 are known and are easily available from the American Type Culture Collection (ATCC). Transformants obtained by using these strains as a host and introducing thereinto plasmids pEDS020 and pSE001 containing gene DNA which codes a protein having the EDDS-ase activity of the strain TN-3 have been deposited as *E. coli* JM109/pEDS020 (FERM BP-6161) and *Rhodococcus rhodochrous* ATCC17895/pSE001 (FERM EP-6548) respectively with National Institute of Bioscience and Human Technology, Agency of Industrial Science and Technology, Ministry of International Trade and Industry.

Methods for preparation of these transformants are described in JP Application No. 9-60077 filed by the present applicant.

Microorganism Having Maleic Acid Isomerase

The microorganism having maleic acid isomerase activity is not particularly limited so long as it is a microorganism capable of iomerizing maleic acid to fumaric acid and may be, for example, microorganisms belonging to the genus Alcaligenes, the genus Pseudomonas, the genus Xanthomonas and the genus Bacillus, and further, transformants obtained by introducing a gene which codes maleic acid isomerase originated from these microorganisms.

Specific examples of the strains include *Alcaligenes faecalis* sp. IFO 12669, *Alcaligenes faecalis* sp. IFO 13111, *Alcaligenes faecalis* sp. IAM1473, *Alcaligenes eutrophas* sp. IAM12305, *Pseudomonas fluolescens* sp. ATCC 23728, *Xanthomonas maltophilia* sp. ATCC13270, Bacillus sp. MI105 (FERM BP-5164), *Bacillus stearothermophirus* sp. MI101 (FERM BP-5160) *Bacillus stearothermophirus* sp. MI102 (FERM BP-5161), *Bacillus brevis* sp. MI103 (FERM BP-5162) and *Bacillus brevis* sp. MI104 (FERM BP-5163).

These microorganisms are easily available from Institute for Fermentation, Osaka (IFO) (a foundation) (Japan); Center for Cellular & Molecular Research IAM Culture Collection, Inst. of Molecular & Cellular Biosciences (Center for Bio-information), University of Tokyo (Japan); the American Type Culture Collection (ATCC) (U.S.A); and National Institute of Bioscience and Human Technology, Agency of Industrial Science and Technology, Ministry of International Trade and Industry (Japan).

Further, among the microorganisms having EDDS-ase, there may also be used microorganisms which have an ability to convert maleic acid into fumaric acid, that is, converts maleic acid and 2-hydroxypropylenediamine directly into S,S-HPDDS. Typical examples of such microorganisms are the above-mentioned Burkholderia sp. KK-5 (FERM BP-5412), Burkholderia sp. KK-9 (FERM BP-5413), Pseudomonas sp. TN-131 (FERM BP-5418), Paracoccus sp. KK-6 (FERM BP-5415), Sphingomonas sp. TN-28 (FERM BP-5419) and Brevundimonas sp. TN-30 (FERM BP-5417). Though microorganisms usable in the present process exist also in the natural world as described above, there may also be used transformants obtained by simultaneously introducing thereinto the maleic acid isomerase gene and the EDDS-ase gene.

The present invention is described in detail below with reference to Examples.

EXAMPLE 1

(1) Preparation of Strain Cell Suspension

One platinum loop of Brevundimonas sp. TN-3 was taken out from a slant culture, inoculated into a culture medium described below and subjected to an aerobic cultivation with shaking at 30° C. for 3 days. Culture medium composition (pH 7.5, 100 ml):

| | |
|---|---|
| ethylenediamine-N,N'-disuccinic acid | 0.2 g |
| glucose | 0.2 g |
| yeast extract | 0.1 g |
| polypeptone | 0.05 g |
| magnesium sulfate.7H$_2$O | 0.1 g |
| sodium sulfate | 0.28 g |
| phosphate buffer solution | 25 mM |
| metal salt mixture solution* | 0.5 ml |

*metal salt mixture solution (100 ml):magnesium chloride.6H$_2$O 8 g, calcium chloride 0.8 g, manganese sulfate.4H$_2$O 0.6 g, ferric chloride.6H$_2$O 0.12 g, zinc sulfate 0.06 g Twenty milliliters of the resulting strain cell culture broth was taken in a centrifuge tube and was subjected to centrifugation at 10,000 rpm at 5° C. for minutes to a harvest the strain cells, which were then washed twice with a 50 mM borate buffer solution, pH 8.0, to prepare a strain cell suspension.

(2) Preparation of Reaction Mixture and Reaction

A reaction mixture containing 200 mM of fumaric acid, 200 mM of 2-hydroxypropylenediamine and the strain cell suspension prepared above and adjusted to pH 8.0 with 6N sodium hydroxide was used and was allowed to react with stirring at 30° C. for 24 hours. As the result, 20 mM of S,S-HPDDS was formed and neither meso isomer nor RR isomer was detected.

The method for determination of S,S-HPDDS concentration was as follows.

After removing insoluble matters in the liquid by means of a centrifugation at 15,000 rpm for 5 min. at 5° C., S,S-HPDDS was determined by liquid chromatography. A column for determination used was WAKOSIL 5C8 (Wako Pure Chemical Industries, Ltd., Japan) (eluent: 50 mM phosphoric acid containing 10 mM of tetra-n-butylammonium hydroxide and 0.4 mM of CuSO$_4$, pH2) and an optical resolution column used was MCI GEL CRS 10W (mfd. by Mitsubishi Chemicals Ltd., Japan) (eluent: 10 mM CuSO$_4$).

Separation and purification of the product was conducted by a technique using an ion exchange resin described in T. Nishikiori et al., J. Antibiotics 37, 426 (1984) and, after collecting crystals, the chemical structure was confirmed by an analysis based on NMR and mass spectrum.

EXAMPLE 2

(1) Preparation of Strain Cell Suspension

Burkholderia sp. KK-5, Burkholderia sp. KK-9, Acidovorax sp. TN-51, Pseudomonas sp. TN-131, Paracoccus sp. KK-6, Paracoccus sp. TNO-5, Sphingomonas sp. TN-28, Brevundimonas sp. TN-30 and Brevundimonas sp. TN-3 were respectively cultivated in the same manner as in Example 1 to prepare strain cell suspensions.

(2) Preparation of Reaction Mixture and Reaction

Reaction mixtures obtained in the same manner as in Example 1 except for using the strain cell suspension prepared above, and reaction mixtures obtained by further adding 100 mM of magnesium sulfate or 100 mM of magnesium chloride to the above-mentioned reaction mixtures were allowed to react with stirring at 30° C. for 15 hours, and the amounts of S,S-HPDDS thus formed were compared with each other.

(3) Results

TABLE 1

| Strain cell | Magnesium salt | Amount of S,S-HPDDS formed (mM) |
|---|---|---|
| TN-3 | No addition | 13.3 |
| | 100 mM magnesium sulfate | 23.5 |
| | 100 mM magnesium chloride | 23.9 |
| | 200 mM magnesium chloride | 30.1 |
| KK-5 | No addition | 4.1 |
| | 100 nM magnesium chloride | 20.2 |
| KK-9 | No addition | 6.7 |
| | 100 mM magnesium chloride | 22.2 |
| TN-51 | No addition | 7.9 |
| | 100 mM magnesium chloride | 14.2 |
| TN-131 | No addition | 11.8 |
| | 100 mM magnesium chloride | 32.0 |
| KK-6 | No addition | 11.1 |
| | 100 mM magnesium chloride | 25.6 |
| TNO-5 | No addition | 2.8 |
| | 100 mM magnesium chloride | 11.2 |
| TN-28 | No addition | 4.1 |
| | 100 mM magnesium chloride | 8.2 |
| TN-30 | No. addition | 18.9 |
| | 100 mM magnesium chloride | 35.1 |

EXAMPLE 3

(1) Preparation of Strain Cell Suspension

One platinum loop of Esherichia coli JM109/pEDS020 was taken out from a slant culture, inoculated into an LB culture medium (1% bacto-tripton, 0.5% bacto-yeast extract, 0.5% NaCl) containing 50 mg/l of ampicillin and subjected to cultivation with shaking at 37° C. for 8 hours. The resulting culture broth was inoculated in an amount of 2.5% into an LB medium (containing 50 ml/l of ampicillin and 1 mM of isopropyl-β-thiogalactoside) and subjected to aerobic cultivation with shaking at 37° C. for 30 hours. From 1,000 ml of the resulting culture broth, the strain cells were harvested by centrifugation (7,000 rpm, 20 min.) and washed once with 500 ml of 50 mM borate buffer solution (pH 7.75) containing 100 mM of 1,4-diaminobutane. The strain cells were resuspended in 500 ml of a similar buffer solution and then, in an ice bath, 25% glutaraldehyde was gradually added to the suspension so as to reach a concentration of 25 mM. Since the pH tended to decrease during the time, the pH was adjusted to 7.75 with 6N NaOH, and then the suspension was allowed to stand with stirring for 2 hours. Ethylenediamine was then added to the suspension so as to reach a concentration of 50 mM, the pH was adjusted to 9.0 with 6N NaOH, and the suspension was allowed to stand for 2 hours. Then sodium borohydride was added so as to reach a concentration of 25 mM and the resulting suspension was allowed to stand with stirring for 2 hours. Then the suspension was adjusted to pH 9.2 with 6N NaOH and then heat-treated in a water bath at 45° C. for 4 hours to obtain a strain cell suspension freed of fumarase activity.

(2) Preparation of Reaction Mixture and Reaction

A reaction mixture was prepared such that the concentrations at the time of initiation of the reaction might be 1,139 mM of fumaric acid, 570 mM of 2-hydroxypropylenediamine and 10 g/l (in terms of dry weight) of strain cells. Water, fumaric acid and 2-hydroxypropylenediamine were mixed in the above-mentioned order with vigorous stirring and adjusted to pH 8.5 with 7.5N NaOH to obtain a transparent reaction mixture. To the reaction mixture was added the strain cell suspension described above to reach a volume of 1,000 ml, and the resulting mixture was allowed to react with stirring at 40° C.

As the result, the concentration of S,S-HPDDS formed after 28 hours was 430 mM.

EXAMPLE 4

(1) Preparation of Strain Cell Suspension

A strain cell suspension was prepared in the same manner as in Example 3.

(2) Preparation of Reaction Mixture and Reaction

A reaction mixture was prepared such that the concentrations at the time of initiation of the reaction might be 1,139 mM of fumaric acid, 570 mM of 2-hydroxypropylenediamine, 570 mM of magnesium hydroxide and 10 g/l (in terms of dry weight) of strain cells. Fumaric acid, magnesium hydroxide and 2-hydroxypropylenediamine were added to water in said order with vigorous stirring and adjusted to pH 8.5 with 7.5 N NaOH to obtain 1,000 ml of a transparent reaction mixture. During the time, the mixture was cooled so that the liquid temperature might not exceed 20° C. It required about 30 minutes for the mixture to reach a complete dissolution. One hour after the addition of 2-hydroxypropylenediamine, the above-mentioned strain cell suspension was added to the mixture to reach a volume of 1,000 ml, and the resulting mixture was allowed to react with stirring at 40° C. Since the pH tended to decrease during the reaction, the pH was kept at 8.5 with an addition of 7.5 N NaOH. At the time of initiation of the reaction, fumaric acid had reacted with 2-hydroxypropylenediamine to form 2-hydroxypropylenediamine-N-monosuccinic acid in an amount of 2 mM as R isomer.

After 28 hours of reaction, the concentration of S,S-HPDDS formed was 494 mM, the concentration of meso-HPDDS was 1 mM, and no HPDDS cyclized product was detected.

EXAMPLE 5

(1) Preparation of Strain Cell Suspension

A strain cell suspension was prepared in the same manner as in Example 3.

(2) Preparation of Reaction Mixture and Reaction

The preparation of a reaction mixture and the reaction were conducted in the same manner as in Example 4 except that the temperature of reaction mixture preparation was changed to 60° C. and the time from the addition of 2-hydroxypropylenediamine to the initiation of reaction was changed to 24 hours (the temperature during the time was 20–30° C.). At 60° C., the mixture could be rapidly brought to a complete dissolution within 5 minutes. The concentration of R-2-hydroxypropylenediamine-N-monosuccinic acid at this time was 42 mM.

After 28 hours, the concentration of S,S-HPDDS formed was 452 mM, the concentration of meso-HPDDS was 38 mM and no HPDDS cyclized product was detected.

EXAMPLE 6

(1) Preparation of Strain Cell Suspension

A strain cell suspension was prepared in the same manner as in Example 3.

(2) Preparation of Reaction Mixture and Reaction

The preparation of the reaction mixture and the reaction were conducted in the same manner as in Example 4.

(3) Insolubilization and Recovery of Magnesium Ion

To a transparent reaction product mixture, from which strain cells had been removed by centrifugation (15,000 rpm, 5 min.), was added 7.5 N NaOH so that the ultimate concentration of NaOH (including NaOH added at the time of reaction mixture preparation and during the reaction) might be 3 times by mole and 4 times by mole, respectively, of the S,S-HPDDS concentration, and the resulting mixtures were allowed to stand with stirring at room temperature for 1 hour. When precipitates originated from magnesium ions thus formed were removed by centrifugation (15,000 rpm, 5 min.), a removal rate of magnesium ions was found to be 52% and 94%, respectively.

(4) Reuse of Recovered Magnesium

A reaction mixture was prepared in the same manner as in Example 4 but by using the magnesium precipitate recovered above. The concentrations of the respective components at the initiation of the reaction were 1,139 mM of fumaric acid, 570 mM of 2-hydroxypropylenediamine, 570 mM of recovered magnesium (concentration in terms of magnesium) and 43 mM of S,S-HPDDS and 10 g/l of strain cells (in terms of dry weight). The reaction mixture was adjusted to pH 8.5 with 7.5 N NaOH and was subjected to a reaction in the same manner as in Example 4.

As the result, no significant difference was observed in the reaction velocity, and the S,S-HPDDS concentration after 28 hours was 523 mM.

EXAMPLE 7

(1) Preparation of Strain Cell Suspension

A strain cell suspension was prepared in the same manner as in Example 3.

(2) Preparation of Reaction Mixture and Reaction

A reaction mixture was prepared in the same manner as in Example 4 except for using 570 mM of iron (III) hydroxide in place of magnesium hydroxide and adjusting pH to 7.5 by use of 7.5 N NaOH. At this time, the iron (III) oxide was dissolved only partly in the reaction mixture.

In the reaction, the pH tended to increase with the progress of reaction unlike in using magnesium hydroxide, and therefore the pH was adjusted by using 5N sulfuric acid. As the result, the concentration of the S,S-HPDDS formed after 24 hours was 472 mM.

(3) Insolubilization and Recovery of Iron (III) Ion

To a transparent centrifugation supernatant obtained by removing strain cells by centrifugation was added, in the same manner as in Example 6, 7.5N NaOH so that the ultimate concentration of NaOH (including NaOH added at the time of the reaction mixture preparation) might be 4 times by mole of the S,S-HPDDS concentration, to insolubilize and recover iron (III) ions. Removal rate of the iron (III) ion was 97%.

(4) Reuse of Recovered Iron (III)

A reaction mixture was prepared by using the recovered precipitate according to the procedures of (2). The concentrations of the respective components at the initiation of the reaction were 1,139 mM of fumaric acid, 570 mM of 2-hydroxypropylenediamine, 570 mM of recovered iron (III) (concentration in terms of iron), 64 mM of S,S-HPDDS and 10 g/l of strain cells (in terms of dry weight). The reaction mixture was subjected to a reaction in the same manner as in (2) above.

As the result, no significant difference was observed in the reaction velocity, and the S,S-HPDDS concentration after 28 hours was 511 mM.

EXAMPLE 8

(1) Preparation of Strain Cell Suspension

A strain cell suspension was prepared in the same manner as in Example 3.

(2) Preparation of Reaction Mixture and Reaction

A reaction mixture was prepared and subjected to a reaction in the same manner as in Example 7 except for using, in place of iron (III) hydroxide, manganese (II) hydroxide of the same molar concentration. As the result, the concentration of the S,S-HPDDS formed after 28 hours was 480 mM.

(3) Insolubilization and Recovery of Manganese (II)

The manganese (II) was insolubilized and recovered in the same manner as in Example 7. Removal rate of the manganese (II) ion was 96%.

(4) Reuse of Recovered Manganese (II)

A reaction mixture was prepared by using the recovered precipitate according to the procedures of (2). The concentrations of the respective components at the initiation of the reaction were 1,139 mM of fumaric acid, 570 mM of 2-hydroxypropylenediamine, 570 mM of the recovered manganese (II) (concentration in terms of manganese), 56 mM of S,S-HPDDS and 10 g/l of strain cells (in terms of dry weight), and the reaction mixture was subjected to a reaction in the same manner as in (2) above. At the time of the reaction mixture preparation, to a brown (due presumably to an oxidation of manganese) suspension resulting from an addition of recovered manganese and fumaric acid to water, was added sodium sulfite powder (about 5% by mole relative to manganese) until a color turned pink, then 2-hydroxypropylenediamine and 7.5N NaOH were added, the resulting mixture was adjusted to pH 7.5 and was allowed to react in the same manner as in (2) above.

As the result, no significant difference was observed in the reaction velocity, and the S,S-HPDDS concentration after 28 hours was 505 mM.

EXAMPLE 9

(1) Preparation of Strain Cell Suspension

A suspension of strain cells of *Esherichia coli* JM 109/pEDS020 was prepared in the same manner as in Example 3.

One platinum loop of *Alcaligenes faecalis* IFO 12669 was taken out from a slant culture, inoculated into 1 l of a maleic acid medium (containing, per 1 l, 5 g of sodium maleate, 10 g of meat extract, 5 g of yeast extract, 5 ml of the metal salt mixture solution described in Example 1 and 50 mM phosphate buffer solution pH 7) and subjected to an aerobic cultivation at 30° C. for 3 days.

The strain cells obtained were harvested by centrifugation (15,000 rpm, 5 min.) and washed twice with 50 mM borate buffer solution, pH 8, to prepare a strain cell suspension.

(2) Preparation of Reaction Mixture and Reaction

A reaction mixture, which contains 300 mM of maleic acid, 100 mM of 2-hydroxypropylenediamine and both of the two strain cell suspensions prepared above (respectively 5 g/l in terms of dry weight) and had been adjusted to pH 8.5 with 7.5 N NaOH, was used. Separately, a reaction mixture was prepared by adding magnesium chloride to a mixture having the same composition as that of the reaction mixture prepared above, so as to attain a concentration of 100 mM. The two reaction mixtures prepared above were compared with each other by subjecting each of them to a reaction with stirring at 30° C. for 24 hours.

Since the pH tended to decrease with the progress of the reaction, pH was maintained at 8.5 by adding 7.5 N NaOH solution with a pH controller. After 24 hours of reaction, the concentration of S,S-HPDDS was 41 mM in a reaction wherein no magnesium chloride was contained and 81 mM in a reaction wherein magnesium chloride was contained.

Referential Example 1

For reference, the change of electric conductivity and of reaction mixture composition during the reaction in Example 4 are shown in Table 2.

The electric conductivity was determined by using an A.C. double-pole electric conductivity indicating controller (Type CDIC-7, mfd. by Toa Denpa Industries, Ltd., Japan) and an electric conductivity cell (Type CGS-3511, ibid.) calibrated with an aqueous KCl solution as a standard.

TABLE 2

| Reaction time (hr) | Electric conductivity (mS/cm) | S,S-HPDDS concentration (mM) | fumaric acid concentration (mM) |
|---|---|---|---|
| 0 | 47.5 | 0 | 1,139 |
| 2 | 45.7 | 41.6 | 943 |
| 4 | 43.0 | 98.9 | 808 |
| 8 | 40.0 | 202 | 584 |
| 16 | 36.4 | 376 | 309 |
| 28 | 33.6 | 494 | 109 |
| 50 | 31.5 | 517 | 32.6 |

EXAMPLE 10

(1) Preparation of Strain Cell Suspension

A strain cell suspension was prepared in the same manner as in Example 3.

(2) Preparation of Reaction Mixture and Reaction

A reaction was conducted in the same manner as in Example 4, which was stopped at the point of time at which the electric conductivity had reached 36.4 mS/cm, to recover and analyze the reaction mixture. As the result, the S,S-HPDDS concentration was 377 mM and the fumaric acid concentration was 306 mM.

EXAMPLE 11

(1) Preparation of Strain Cell Suspension

A strain cell suspension was prepared in the same manner as in Example 3.

(2) Preparation of Reaction Mixture and Reaction

A reaction was started with the same composition and conditions as in Example 4, with a reaction volume of 1,000 ml. When the electric conductivity had reached 36.4 mS/cm, a reaction mixture of the same composition was fed with a tube pump and simultaneously a part of the reaction mixture was recovered so as to keep the electric conductivity within the range of 33.4–33.8 mS/cm and the liquid volume within the range of 980 ml–1,020 ml. In the recovery, a gear pump and a hollow fiber membrane (SF-8102, mfd. by Kuraray Co., Ltd., Japan, pore diameter 0.1 μm, inner diameter× length=1.2×350 mm) were used so that the strain cells could be returned to the reaction vessel and the filtrate alone could be recovered.

The above-mentioned operations were conducted for 100 hours, during which the S,S-HPDDS concentration was in the range of 487–494 mM, the fumaric acid concentration was in the range of 106–115 mM and the starting material feed rate was 18.6 ml/hr in an average.

EXAMPLE 12

(1) Preparation of Strain Cell Suspension

A strain cell suspension was prepared in the same manner as in Example 3.

(2) Preparation of Reaction Mixture and Reaction

A reaction mixture was prepared and subjected to a reaction in the same manner as in Example 4.

(3) Recovery of S,S-HPDDS

One hundred milliliters of a transparent reaction product mixture, from which strain cells had been removed by centrifugation (15,000 rpm, 5 min.), was brought to 60° C., and then 47% sulfuric acid was added thereto to adjust pH to 2.6. Thereafter, the liquid was kept at 60° C. for 30 minutes and then gradually cooled over 2 hours until the temperature reached 20° C. During the time, since the pH increased, it was kept in the range of pH 2.4–2.8 with 47% sulfuric acid. Precipitated crystals were filtered with a Buchner funnel and washed with demineralized water in amount of about one tenth weight thereof. S,S-HPDDS crystals obtained by drying at 80° C. for 15 hours had a recovery rate from the reaction product mixture of 90%, the amount of HPDDS cyclized products was 0.1% by mole or less relative to S,S-HPDDS and the amount of HPDDS cyclized products in the supernatant was 3% by mole relative to the initial S,S-HPDDS.

EXAMPLE 13

(1) Preparation of Strain Cell Suspension

A strain cell suspension was prepared in the same manner as in Example 3.

(2) Preparation of Reaction Mixture and Reaction

A reaction mixture was prepared and subjected to a reaction in the same manner as in Example 4.

(3) Recovery of S,S-HPDDS

One hundred milliliters of a transparent reaction product mixture, from which strain cells had been removed by centrifugation (15,000 rpm, 5 min.), was brought to 20° C. and adjusted to pH 3.0 by an addition of 47% sulfuric acid. Into the resulting solution was fed the above-mentioned reaction mixture at a rate of 30 ml/hr. Simultaneously therewith, the slurry was withdrawn so as to keep the inner liquid volume at 100 ml (residence time: 3.3 hours) and, at the same time, the pH was kept in the range of pH 2.4–2.8 with 47% sulfuric acid. After 24 hours, a part of the precipitated crystals was filtered with a Buchner funnel and washed with demineralized water in amount of about one tenth weight thereof. Recovery rate from the reaction product mixture of S,S-HPDDS crystals dried at 80° C. for 15 hours was 92%, which crystals contained no HPDDS cyclized product, and the amount of HPDDS cyclized product in the supernatant was 0.1% by mole relative to the initial S,S-HPDDS.

EXAMPLE 14

(1) Preparation of Strain Cell Suspension

A strain cell suspension was prepared in the same manner as in Example 3.

(2) Preparation of Reaction Mixture and Reaction

A reaction mixture was prepared and subjected to a reaction in the same manner as in Example 3.

(3) Recovery of S,S-HPDDS

To 1,000 ml of a transparent reaction product mixture, from which strain cells had been removed by centrifugation (15,000 rpm, 5 min.), was added 950 mmol of fumaric acid, and the resulting mixture was stirred for 30 minutes and then was cooled to 15° C. and stirred for 1 hour. The precipitated crystals were filtered with a Buchner funnel and washed with demineralized water in amount of about one tenth weight thereof. Recovery rate from the reaction product mixture of the S,S-HPDDS crystals dried at 80° C. for 15 hours was 52%.

(4) Reuse of S,S-HPDDS Recovery Supernatant

The supernatant obtained in the above-mentioned recovery was used to prepare a reaction mixture according to the procedure of (2). The concentrations of the respective components at the initiation of the reaction were 1,139 mM of fumaric acid, 570 mM of 2-hydroxypropylenediamine, 196 mM of S,S-HPDDS and 10 g/l of strain cells (in terms of dry weight). The reaction mixture was subjected to a reaction in the same manner as in (2).

As the result, the concentration of the S,S-HPDDS formed after 28 hours was 619 mM.

EXAMPLE 15

(1) Preparation of Strain Cell Suspension

A strain cell suspension was prepared in the same manner as in Example 3.

(2) Preparation of Reaction Mixture and Reaction

A reaction mixture was prepared such that the concentrations at the initiation of the reaction might be 1,139 mM of fumaric acid, 570 mM of 2-hydroxypropylenediamine, 855 mM of magnesium hydroxide and 10 g/l of strain cells (in terms of dry weight). To water were added fumaric acid, magnesium hydroxide and 2-hydroxypropylenediamine in said order with vigorous stirring to obtain 1,000 ml of a transparent reaction mixture (pH about 9). During the time, the mixture was cooled so that the liquid temperature might not exceed 20° C., and it required about 30 minutes for the mixture to reach a complete dissolution. One hour after the addition of 2-hydroxypropylenediamine, the above-mentioned strain cell suspension was added, the resulting mixture was made up to a volume of 1,000 ml and allowed to react with stirring at 40° C. During the reaction, since the pH decreased, pH was kept at 8.5 by an addition of 7.5 N NaOH. At the time of initiation of the reaction, 2-hydroxypropylenediamine-N-monosuccinic acid had been formed, in a concentration of 2 mM as R isomer, from fumaric acid and 2-hydroxypropylenediamine.

After 28 hours of reaction, the concentration of the S,S-HPDDS formed was 510 mM, that of meso-HPDDS was 1 mM and no HPDDS cyclized product was detected.

To the reaction product mixture thus obtained were further added fumaric acid and 2-hydroxypropylenediamine each in an amount corresponding to half the amount which existed at the initiation of the reaction. During the time, the pH was maintained in the range of 8–9 by use of 7.5 N NaOH and ultimately adjusted to 8.5. During the addition, the mixture was cooled so that the liquid temperature might not exceed 40° C. It required about 15 minutes for the mixture to reach a complete dissolution. The concentration of 2-hydroxypropylenediamine-N-monosuccinic acid at this time was 1 mM as R isomer.

After 15 hours (including a period of time of a preparation required for further addition of the starting materials), the concentration of the S,S-HPDDS formed was 667 mM, that of meso-HPDDS was 2 mM and no HPDDS cyclized product was detected.

Industrial Applicability

According to the present invention, S,S-HPDDS can be stereospecifically synthesized from fumaric acid and 2-hydroxypropylenediamine by the action of EDDS-ase and, further, from maleic acid and 2-hydroxypropylenediamine by combining the action of EDDS-ase with the action of maleic acid isomerase, under mild conditions of ordinary temperature and ordinary pressure in an industrially advantageous way without using expensive optically active substances.

What is claimed is:

1. A process for producing S,S-2-hydroxypropylenediamine-N,N'-disuccinic acid which comprises contacting fumaric acid and 2-hydroxypropylenediamine as substrates in an aqueous medium containing ethylenediamine disuccinic acid ethylenediamine lyase to form a reaction product mixture, and producing S-S,2-hydroxypropylenediamine-N,N'-disuccinic acid from said substrates by the action of ethylenediamine disuccinic acid ethylenediamine lyase.

2. A process for producing S,S-2-hydroxypropylenediamine-N,N'-disuccinic acid which comprises contacting maleic acid or maleic anhydride and 2-hydroxypropylenediamine as substrates in an aqueous medium containing ethylenediamine disuccinic acid ethylenediamine lyase and maleic acid isomerase to form a reaction product mixture, and producing S-S-2-hydroxypropylenediamine-N-N'-disuccinic acid from said substrates by combined actions of ethylenediamine disuccinic acid ethylenediamine lyase and maleic acid isomerase.

3. The process for producing S,S-2-hydroxypropylenediamine-N, N'-disuccinic acid according to claim 1 wherein at least one metal ion selected from the group consisting of alkaline earth metals, iron, zinc, copper, nickel, aluminum, titanium and manganese is present in the aqueous medium containing the substrates.

4. The process for producing S,S-2-hydroxypropylenediamine-N,N'-disuccinic acid according to claim 3 wherein the metal ion is at least one metal ion selected from the group consisting of magnesium, manganese and iron.

5. The process for producing S,S-2-hydroxypropylenediamine-N,N'-disuccinic acid according to claim 1 wherein R-2-hydroxypropylenediamine-N-monosuccinic acid is an impurity in the aqueous medium and is present at 2.5% by mole or less of the theoretical value of S,S-2-hydroxypropylenediamine-N,N'-disuccinic acid to be formed.

6. A process for producing an S,S-2-hydroxypropylenediamine-N,N'-disuccinic acid alkali metal salt which comprises adding an alkali hydroxide to the reaction product mixture obtained in claim 3 to separate and recover as an insoluble precipitate the at least one metal ion and to simultaneously convert the S,S-2-hydroxypropylenediamine-N,N'-disuccinic acid into its alkali metal salt.

7. The process for producing S-S-2-hydroxypropylenediamine-N-N'-disuccinic acid according to claim 6 wherein the separated and recovered insoluble precipitate is reused as a metal ion source.

8. The process for producing S,S-2-hydroxypropylenediamine-N,N'-disuccinic acid according to claim 1 which comprises adding at least one organic acid selected from the group consisting of fumaric acid, maleic acid and maleic anhydride to the reaction product mixture, recovering S,S-2-hydroxypropylenediamine-N,N'-disuccinic acid or its salt as an insoluble substance and reusing a resulting supernatant for a reaction.

9. The process for producing S,S-2-hydroxypropylenediamine-N,N'-disuccinic acid according to claim 1 further comprising precipitating and recovering S,S-2-hydroxypropylenediamine-N,N'-disuccinic acid as crystalline powder from the reaction product mixture under an acidic condition with a mineral acid.

10. The process for producing S,S-2-hydroxypropylenediamine-N,N'-disuccinic acid according to claim 1 wherein the ethylenediamine disuccinic acid ethylenediamine lyase is from a microorganism belonging to the genus Brevundimonas, the genus Paracoccus, the genus Sphingomonas, the genus Acidovorax, the genus Pseudomonas, the genus Burkholderia or a microorganism containing a gene DNA which encodes ethylenediamine disuccinic acid ethylenediamine lyase from these microorganisms.

11. The process for producing S,S-2-hydroxypropylenediamine-N,N'-disuccinic acid according to claim 2 wherein the ethylenediamine disuccinic acid ethylenediamine lyase is from a microorganism belonging to the genus Brevundimonas, the genus Paracoccus, the genus Sphingomonas, the genus Acidovorax, the genus Pseudomonas, the genus Burkholderia or a microorganism containing a gene DNA which encodes ethylenediamine disuccinic acid ethylenediamine lyase from these microorganisms and the maleic acid isomerase is from a microorganism belonging to the genus Alcaligenes, the genus Pseudomonas, the genus Xanthomonas, the genus Bacillus or from a microorganism containing a gene DNA which encodes maleic acid isomerase from these microorganisms.

12. The process for producing S,S-2-hydroxypropylenediamine-N,N'-disuccinic acid according to claim 2 wherein at least one metal ion selected from the group consisting of alkaline earth metals, iron, zinc, copper, nickel, aluminum, titanium and manganese is present in the aqueous medium containing the substrates.

13. The process for producing S,S-2-hydroxypropylenediamine-N,N'-disuccinic acid according to claim 12 wherein the metal ion is at least one metal ion selected from the group consisting of magnesium, manganese and iron.

14. The process for producing S,S-2-hydroxypropylenediamine-N,N'-disuccinic acid according to claim 2 wherein R-2-hydroxypropylenediamine-N-monosuccinic acid is an impurity in the aqueous medium and is present at 2.5% by mole or less of the theoretical value of S,S-2-hydroxypropylenediamine-N,N'-disuccinic acid to be formed.

15. A process for producing an S,S-2-hydroxypropylenediamine-N,N'-disuccinic acid alkali metal salt which comprises adding an alkali hydroxide to the reaction product mixture obtained in claim 12 to separate and recover as an insoluble precipitate the at least one metal ion and to simultaneously convert the S,S-2-hydroxypropylenediamine-N,N'-disuccinic acid into its alkali metal salt.

16. A process for producing an S,S-2-hydroxypropylenediamine-N,N'-disuccinic acid alkali metal salt which comprises adding an alkali hydroxide to the reaction product mixture obtained in claim 4 to separate and recover as an insoluble precipitate the at least one metal ion and to simultaneously convert the S,S-2-hydroxypropylenediamine-N,N'-disuccinic acid into its alkali metal salt.

17. A process for producing an S,S-2-hydroxypropylenediamine-N,N'-disuccinic acid alkali metal salt which comprises adding an alkali hydroxide to the reaction product mixture obtained in claim 13 to separate and recover as an insoluble precipitate the at least one metal ion and to simultaneously convert the S,S-2-hydroxypropylenediamine-N,N'-disuccinic acid into its alkali metal salt.

18. The process for producing S-S-2-hydroxypropylenediamine-N-N'-disuccinic acid according to claim 15 wherein the separated and recovered insoluble precipitate is reused as a metal ion source.

19. The process for producing S-S-2-hydroxypropylenediamine-N-N'-disuccinic acid according to claim 16 wherein the separated and recovered insoluble precipitate is reused as a metal ion source.

20. The process for producing S-S-2-hydroxypropylenediamine-N-N'-disuccinic acid according to claim 17 wherein the separated and recovered insoluble precipitate is reused as a metal ion source.

21. The process for producing S,S-2-hydroxypropylenediamine-N,N'-disuccinic acid according to claim 2 which comprises adding at least one organic acid selected from the group consisting of fumaric acid, maleic acid and maleic anhydride to the reaction product mixture, recovering S,S-2-hydroxypropylenediamine-N,N'-disuccinic acid or its salt as an insoluble substance and reusing a resulting supernatant for a reaction.

22. The process for producing S,S-2-hydroxypropylenediamine-N,N'-disuccinic acid according to claim 2 further comprising precipitating and recovering S,S-2-hydroxypropylenediamine-N,N'-disuccinic acid as crystalline powder from the reaction product mixture under an acidic condition with a mineral acid.

* * * * *